United States Patent [19]

Knuth et al.

[11] Patent Number: 5,990,358
[45] Date of Patent: Nov. 23, 1999

[54] PROCESS FOR THE PREPARATION OF FORMALDEHYDE

[75] Inventors: Bernhard Knuth, Ludwigshafen; Rainer Diercks, Neuhofen, both of Germany

[73] Assignee: BASF Aktiengesellschaft, Ludwigshafen, Germany

[21] Appl. No.: 09/029,853

[22] PCT Filed: Feb. 11, 1997

[86] PCT No.: PCT/EP97/00615

§ 371 Date: Mar. 13, 1998

§ 102(e) Date: Mar. 13, 1998

[87] PCT Pub. No.: WO97/30015

PCT Pub. Date: Aug. 21, 1997

[30] Foreign Application Priority Data

Feb. 13, 1996 [DE] Germany .......................... 196 05 213

[51] Int. Cl.$^6$ .................................................. C07C 45/00
[52] U.S. Cl. .......................... 568/473; 568/471; 568/472
[58] Field of Search ..................... 568/473, 471, 568/472

[56] References Cited

U.S. PATENT DOCUMENTS

| | | | |
|---|---|---|---|
| 2,462,413 | 2/1949 | Meath | 568/473 |
| 2,587,468 | 2/1952 | Heider | 260/348.5 |
| 3,948,997 | 4/1976 | Howe et al. | 568/402 |
| 3,959,385 | 5/1976 | Nienburg et al. | 568/454 |
| 3,991,118 | 11/1976 | Diem et al. | 568/473 |
| 4,098,826 | 7/1978 | Alpers et al. | 568/473 |
| 4,167,527 | 9/1979 | Nielsen | 568/473 |
| 4,198,351 | 4/1980 | Branecky et al. | 568/473 |
| 4,219,509 | 8/1980 | Nielsen et al. | 568/473 |
| 4,383,123 | 5/1983 | Ferris et al. | 568/473 |
| 4,439,625 | 3/1984 | Rao | 568/473 |
| 5,854,163 | 12/1998 | Diercks et al. | |

*Primary Examiner*—James O. Wilson
*Attorney, Agent, or Firm*—Oblon, Spivak, McClelland, Maier & Neustadt, P.C.

[57] ABSTRACT

A process for preparing formaldehyde by oxidative dehydrogenation of methanol comprises passing a gas mixture (i) comprising a) from 0.1 to 50% by volume of methanol,
b) from 0.1 to 30% by volume of oxygen,
c) from 0 to 50% by volume of nitrogen oxide and
d) from 0 to 60% by volume of water at from 150 to 800° C. through a phosphorus-doped silver catalyst fixed bed (a) and applying from 0.01 to 100 ppm by weight of phosphorus, based on the phosphorus-doped silver catalyst fixed bed, in the form of a finely divided phosphorus compound having a melting point or decomposition temperature of more than 500° C. (phosphorus compound P) to the phosphorus-doped silver catalyst fixed bed (a) per kg of methanol which is passed through in the form of the gas mixture (i) per $cm^2$ of the cross-sectional area of the phosphorus-doped silver catalyst fixed bed (a).

4 Claims, No Drawings

PROCESS FOR THE PREPARATION OF FORMALDEHYDE

BACKGROUND OF THE INVENTION

1. Field of the Invention

The present invention relates to a process for preparing formaldehyde by oxidative dehydrogenation of methanol.

2. Description of the Background

Processes for preparing formaldehyde by oxidative dehydrogenation of methanol over a catalyst fixed bed made up of silver crystals are generally known (cf. Ullmanns Enzyklopädie der technischen Chemie, 3rd Edition, Urban und Schwarzenberg, Munich/Berlin, 1956, Volume 7, pages 660 to 663).

Advantageous effects which occur when using phosphorus compounds as promoters for the oxidation of methanol to give formaldehyde in the presence of a silver catalyst are also known from CN-A-85100530, DE-A-4022603 and JP-A-38227/83.

EP-A-0 467 169 describes the preparation of formaldehyde by oxidative dehydrogenation of methanol over a catalyst fixed bed which is made up of layers of silver crystals containing a pulverulent phosphorus-containing salt as promotor. This phosphorus-doped silver catalyst fixed bed is prepared by bringing it into contact with a phosphorus compound prior to the commencement of the formaldehyde preparation.

However, these processes are still capable of improvement because the catalyst continuously loses activity during use for the formaldehyde preparation, which is reflected in a decreasing yield. For this reason, the catalyst has to be replaced and regenerated after a relatively short time, for which purpose the formaldehyde preparation process has to be interrupted. Since the replacement of the catalyst fixed bed and the measures associated with the resumption of the formaldehyde preparation process are time-consuming and laborious, the economics of the process depend on how frequently this replacement has to be carried out.

SUMMARY OF THE INVENTION

It is an object of the present invention to develop a process in which the time between the required replacement of the catalyst is prolonged.

We have found that this object is achieved by a process for preparing formaldehyde by oxidative dehydrogenation of methanol, which comprises passing a gas mixture (i) comprising a) from 0.1 to 50% by volume, preferably from 10 to 40% by volume, of methanol, b) from 0.1 to 30% by volume, preferably from 5 to 20% by volume, of oxygen, c) from 0 to 50% by volume, preferably from 1 to 20% by volume, of nitrogen oxide and d) from 0 to 60% by volume, preferably from 10 to 50% by volume, of water at from 150 to 800° C. through a phosphorus-doped silver catalyst fixed bed (a) and applying from 0.01 to 100 ppm by weight of phosphorus, based on the phosphorus-doped silver catalyst fixed bed, in the form of a finely divided phosphorus compound having a melting point or decomposition temperature of more than 500° C. (phosphorus compound P) to the phosphorus-doped silver catalyst fixed bed (a) per kg of methanol which is passed through in the form of the gas mixture (i) per $cm^2$ of the cross-sectional area of the phosphorus-doped silver catalyst fixed bed (a).

DETAILED DESCRIPTION OF THE INVENTION

These data are based on a pressure of 1 bar.

The gas mixture generally contains from 0.25 to 0.60, preferably from 0.35 to 0.50, mol of oxygen per mol of methanol and from 0.2 to 3.0, preferably from 0.67 to 1.75, mol of water per mol of methanol and from 0.9 to 2.3, preferably from 1.3 to 1.8, mol of nitrogen per mol of methanol.

Phosphorus-doped silver catalysts suitable for the process of the present invention are, for example, those obtainable by I. arranging silver crystals which are obtained by electrolytic deposition of silver from an aqueous silver salt solution to form a starting silver catalyst fixed bed (a), and subsequently II. bringing the starting silver catalyst fixed bed (a) into contact with from 1 to 20,000 ppm by weight of phosphorus, based on the silver, in the form of the phosphorus compound (P) before the gas mixture (i) is passed at from 150 to 800° C. through the fixed bed.

The preparation of the silver crystals described in step I is generally known (cf. Ullmann's Enzyklopädie der technischen Chemie, 3rd Edition, Urban und Schwarzenberg, Munich/Berlin, 1956, Volume 7, pages 660 to 663). Particularly good results can be achieved using the starting catalyst fixed beds described in DE-A-2322757.

Suitable silver crystals are obtained particularly when the electrolysis is carried out according to the process described in the German Patent 1166171.

As electrolyte, preference is given to using an aqueous silver nitrate solution. This silver nitrate solution generally has a pH of from 1 to 4 and contains from 1 to 5% by weight of silver. The pH is advantageously adjusted using nitric acid.

The electrodes employed are those customarily used in the electrolysis of silver. Suitable anodes are sacks which have been charged with the silver to be oxidized, generally as granules or powder. Suitable cathodes are, in particular, silver sheets.

The electrolysis is advantageously carried out at current densities of from 80 to 500 $A/m^2$ of cathode area and electrolyte temperatures of from 10 to 30° C.

To achieve these current densities, voltages of from 1 to 15 volts are necessary in most electrolysis cells.

It is advisable to continually remove the silver crystals formed from the cathode. Silver crystals having a particle size of from 0.2 to 5 mm are generally obtained.

A single electrolysis is usually sufficient to obtain usable silver crystals.

In general, the silver crystals are arranged to form a starting silver catalyst fixed bed (a) which comprises from 1 to 9 layers of silver crystals and has a total bed thickness of from 1 to 10 cm. Such fixed beds which are also designated as short beds are generally known (cf. Ullmanns Enzyklopädie der technischen Chemie, 4th Edition, Verlag Chemie, Weinheim-N.Y., Volume 13, pages 539 to 541).

In step II, the starting silver catalyst fixed bed (a) is brought into contact with from 1 to 20,000 ppm by weight, preferably from 5 to 5000 ppm by weight, of phosphorus, based on the silver, in the form of a finely divided phosphorus compound having a melting point or decomposition temperature of more than 500° C. (phosphorus compound P).

Suitable phosphorus compounds (P) are phosphorus-containing salts. Examples of these are the phosphorus-containing salts mentioned in DE-A-4022603, e.g. inorganic phosphates of alkali metals, alkaline earth metals and heavy metals such as Ag, Zn and Fe or of boron and ammonium.

Preference is given to phosphates or pyrophosphates of alkali metals or alkaline earth metals, e.g. $Na_4P_2O_7$, $Li_3PO_4$, $Mg_3(PO_4)_2$, $Ca_3(PO_4)_2$.

In general, the procedure is to sprinkle a finely divided powder of the phosphorus compound (P) onto the silver catalyst fixed bed or to impregnate the silver catalyst fixed bed with a solution of the phosphorus compound (P) and to allow the solvent to evaporate.

The particle size of the phosphorus compound (P) used as powder is not critical; it is generally from about 1 mm to 1 µm. The solutions of the phosphorus compounds (P) are generally aqueous solutions containing from 0.01 to 50% by weight of the phosphorus compound (P). To impregnate the silver catalyst fixed bed, it is soaked with one of the solutions or, particularly advantageously, the solutions are sprayed onto the silver catalyst fixed bed to be activated and the solvent is subsequently evaporated.

The amount of phosphorus compound (P) sprayed on or sprinkled on is preferably selected such that the amount of phosphorus is from 0.01 to 100, preferably from 0.05 to 10, mg per $cm^2$ of the cross-sectional area of the phosphorus-doped silver catalyst fixed bed.

The silver catalyst fixed beds (a) produced in this way generally do not display their full catalytic activity at the commencement of the passing through of the gas mixture (i). It has therefore been found to be advantageous to activate the phosphorus-doped silver catalyst fixed beds (a) at the commencement of the formaldehyde preparation.

The activation of the catalyst can, for example, be carried out by preheating the catalyst to from 300 to 400° C. immediately before the commencement of the passing through of the gas mixture (i) and/or passing a gas mixture (i) preheated to from 100 to 800° C., preferably from 200 to 700° C., through the fixed bed. The amount of methanol in the form of the gas mixture (i) which is passed through the phosphorus-doped silver catalyst fixed bed (a) at the commencement of the activation phase, which usually takes from 0.1 to 100 hours, per hour and per $cm^2$ of cross-sectional area of this silver catalyst fixed bed is from 0.001 to 1 kg. The amount of gas mixture (i) which is passed per unit time through the phosphorus-doped silver catalyst fixed bed (a) is continuously increased during the activation phase to the final value which is generally from 0.1 to 1 kg. In general, the preheating of the gas mixture (i) becomes superfluous at the latest after the end of the activation phase, since the fixed bed is heated to the required temperature by the heat of reaction which is liberated.

To enable the activation phase and the preparation of formaldehyde by the process of the present invention to follow one another without a break, the activation of the starting catalyst fixed bed (a) is advantageously carried out in a fixed-bed reactor as is customarily used for the preparation of formaldehyde by oxidative dehydrogenation of methanol and the gas mixture (i) is continuously passed through this. The reactor is here preferably vertical and the gas mixture (i) is passed through the reactor from the top downward. Such reactors and processes are described, for example, in EP-A-467 169, DE-A-2444586 and EP-A-0150436.

The cross-sectional area of the reactor and the starting silver catalyst fixed bed (a) are advantageously selected so as to be the same and the catalyst fixed bed is arranged in the reactor so that the layers of the silver crystals are perpendicular to the flow direction of the gas mixture (i).

The phosphorus-doped silver catalyst fixed beds (a) have their activity maximum at the end of the activation phase and slowly and steadily lose activity during use in the process of the present invention, which becomes apparent from a falling yield of formaldehyde.

This activity loss for the phosphorus-doped silver catalyst fixed beds (a) can be partially avoided if from 0.01 to 100 ppm by weight of phosphorus, based on the phosphorus-doped silver catalyst fixed bed (a), in the form of the phosphorus compound (P) per kg of methanol in the form of the gas mixture (i) which, based on 1 $cm^2$ of the cross-sectional area of the phosphorus-doped silver catalyst fixed bed, is passed through the latter, is applied to the silver catalyst fixed bed, either continuously or discontinuously (in each case in one portion after introduction of a defined amount of gas mixture (i)), preferably without interrupting the introduction of the gas mixture (i). In the case of continuous application, the activity loss can be slowed down; in the case of the stepwise, discontinuous application, the activity loss can be partially reversed.

If the subsequent application of the phosphorus compound (P) is carried out discontinuously, the intervals between the applications of the phosphorus compound (P) to the phosphorus-doped silver catalyst fixed bed are selected such that during this time not more than 500, preferably from 1 to 5, kg of methanol in the form of the gas mixture (i), based on 1 $cm^2$ of the cross-sectional area of the phosphorus-doped silver catalyst fixed bed, are passed through the catalyst fixed bed, since otherwise the yield would drop too much in the meantime.

Otherwise, the preparation process for formaldehyde by oxidative dehydrogenation of methanol using the catalyst fixed bed of the present invention is carried out in a manner known per se, by passing the gas mixture (i) at from about 500 to 750° C., in particular from 600 to 710° C., through the phosphorus-doped silver catalyst fixed bed. The process is generally carried out continuously at a pressure of from 0.5 to 2 bar, preferably from 0.8 to 1.8 bar. It is here advantageous to cool the reaction gases leaving the catalyst zone within a short time, for example to from 50 to 350° C.

Preferably, the phosphorus-doped silver catalyst fixed bed is located in a vertical reactor and the gas mixture (i) is passed through the reactor from the top downward. Advantageously, the cross-sectional area of the reactor and that of the starting silver catalyst fixed bed (a) are selected so as to be equal and the catalyst fixed bed is arranged in the reactor so that the layers of the silver crystals are perpendicular to the flow direction of the gas mixture (i).

The cooled gas mixture is then advantageously conveyed to an absorption tower in which the formaldehyde is scrubbed from the gas mixture using water or an aqueous formaldehyde/urea solution.

Specific advantageous variants of the generally known process for preparing formaldehyde which can also be employed in the process of the present invention are recommended in DE-A-2444586, DE-A-2451990, EP-A-0083427 and EP-A-0150436.

The process of the present invention is notable, in particular, for the fact that it enables formaldehyde to be prepared particularly economically, because in this process the yield and the selectivity in the oxidative dehydrogenation of methanol is particularly high over a long period of time.

EXAMPLE 1

In a vertical experimental reactor having an internal diameter of 15 cm, a three-layer starting silver catalyst fixed bed having the same diameter and a total bed thickness of 2 cm was installed. The lower layer comprised 1000 g of silver crystals having a particle size of from 1 to 2.5 mm, the middle layer comprised 65 g of silver crystals having a particle size of from 0.75 to 1 mm and the upper layer comprised 185 g of silver crystals having a particle size of from 0.2 to 0.75 mm.

Phosphorus in the form of pulverulent $Na_4P_2O_7$ was sprinkled on the surface of the staring silver catalyst fixed bed in an amount of 1.3 mg of phosphorus (calculated as elemental phosphorus) per $cm^2$ of cross-sectional area of the fixed bed. The phosphorus-doped silver catalyst fixed bed thus produced was heated to 360° C. Subsequently, to activate the catalyst, a gas mixture comprising methanol, air and water was passed through the catalyst. During the 28-hour activation period, the amount was increased to 32 kg of methanol, 21.4 kg of water and 54 kg of air per hour (final throughput). The temperature in the fixed bed was 700° C. at the end of the activation period. This feed flow was kept constant during the entire time of the experiment.

During the continuous operation of the reactor, further amounts in phosphorus in the form of pulverulent $Na_4P_2O_7$ were applied to the phosphorus-doped silver catalyst fixed bed after the operating times indicated in Table 1 (operating day 0 is the point in time immediately after the activation of the catalyst). The respective amounts are given in Table 1 (cumulative amounts).

TABLE 1

| Operating days | Amount of phosphorus [g/cm²] | Yield [%] |
| --- | --- | --- |
| 0 | 1.3 | 90.1 |
| 4 | 1.3 | 89.7 |
| 6 | 1.42 | 90.1 |
| 9 | 1.42 | 89.6 |
| 11 | 1.61 | 90.0 |
| 16 | 1.61 | 89.3 |
| 17 | 1.70 | 89.9 |

We claim:

1. A process for preparing formaldehyde by oxidative dehydrogenation of methanol, which comprises passing a gas mixture (i) comprising a) from 0.1 to 50% by volume of methanol, b) from 0.1 to 30% by volume of oxygen, c) from 0 to 50% by volume of nitrogen oxide and d) from 0 to 60 % by volume of water at from 150 to 800° C. through a phosphorus-doped silver catalyst fixed bed (a) and applying from 0.01 to 100 ppm by weight of phosphorus, based on the phosphorus-doped silver catalyst fixed bed in the form of a finely divided phosphorus compound (P) having a melting point or decomposition temperature of more than 500° C., to the phosphorus-doped silver catalyst fixed bed (a) per kg of methanol which is passed through in the form of the gas mixture (i) per $cm^2$ of the cross-sectional area of the phosphorus-doped silver catalyst fixed bed (a).

2. A process as claimed in claim 1, wherein the phosphorus-doped silver catalyst fixed bed (a) used is obtainable by I. arranging silver crystals which are obtained by electrolytic deposition of silver from an aqueous silver salt solution to form a starting silver catalyst fixed bed (a), and subsequently II. bringing the starting silver catalyst fixed bed (a) into contact with from 1 to 20,000 ppm by weight of phosphorus, based on the silver, in the form of the phosphorus compound (P) before the gas mixture (i) is passed at from 150 to 800° C. through the fixed bed.

3. A process as claimed in claim 1, wherein the phosphorus-doped silver catalyst fixed bed (a) used is made up of one or more layers of silver crystals whose longest mean diameter is from 0.2 to 10 mm and the total bed thickness is from 1 to 10 cm.

4. A process as claimed in claim 1, wherein the phosphorus compound (P) used is a phosphate or pyrophosphate of an alkali metal or alkaline earth metal.

* * * * *